(12) United States Patent
Koda et al.

(10) Patent No.: US 6,923,760 B2
(45) Date of Patent: Aug. 2, 2005

(54) ENDOSCOPIC AUDITORY CANAL CLEANING APPARATUS

(75) Inventors: Yoshiharu Koda, Tokyo (JP); Kojiro Koda, Tokyo (JP)

(73) Assignee: Coden Co., Ltd. (JP)

( * ) Notice: Subject to any disclaimer, the term of this patent is extended or adjusted under 35 U.S.C. 154(b) by 35 days.

(21) Appl. No.: 10/679,519

(22) Filed: Oct. 6, 2003

(65) Prior Publication Data

US 2004/0249244 A1 Dec. 9, 2004

(30) Foreign Application Priority Data

Jun. 6, 2003 (JP) ........................................ 2003-162942

(51) Int. Cl.[7] ............................................. A61B 1/267
(52) U.S. Cl. ..................... 600/200; 600/127; 600/199; 606/161; 606/162; 604/1
(58) Field of Search ................................ 600/199–200, 600/127, 129, 104, 101, 562, 569; 606/161, 162; 604/1–3

(56) References Cited

U.S. PATENT DOCUMENTS

| 3,638,643 | A | | 2/1972 | Hotchkiss |
| 4,785,796 | A | * | 11/1988 | Mattson ...................... 600/200 |
| 5,060,632 | A | | 10/1991 | Hibino et al. |
| 5,209,757 | A | | 5/1993 | Krug et al. |
| 5,325,847 | A | | 7/1994 | Matsuno |
| 5,762,605 | A | | 6/1998 | Cane et al. |
| 5,888,199 | A | | 3/1999 | Karell et al. |
| 5,916,150 | A | | 6/1999 | Sillman |
| 5,938,590 | A | | 8/1999 | Elliott |
| 5,961,441 | A | | 10/1999 | Plumb et al. |
| 6,059,719 | A | | 5/2000 | Yamamoto et al. |
| 6,093,155 | A | | 7/2000 | Ouchi |
| 6,155,987 | A | | 12/2000 | Scherl |
| 6,306,084 | B1 | * | 10/2001 | Pinczower .................. 600/184 |
| 6,500,114 | B1 | | 12/2002 | Petitto et al. |
| 6,699,178 | B1 | * | 3/2004 | Koda .......................... 600/104 |
| 2003/0187331 | A1 | * | 10/2003 | Faludi et al. ............... 600/200 |

FOREIGN PATENT DOCUMENTS

| JP | HEI2(1990)-132494 | 11/1990 |
| JP | HEI6(1994)-269474 | 9/1994 |
| JP | HEI8(1996)-173382 | 7/1996 |
| WO | WO-97/33530 | 9/1997 |

OTHER PUBLICATIONS

U.S. Appl. No. 09/713,723, filed Nov. 15, 2000, Koda.

* cited by examiner

Primary Examiner—Beverly M. Flanagan
Assistant Examiner—Matthew Kasztejna
(74) Attorney, Agent, or Firm—Synnestvedt Lechner & Woodbridge, LLP; Roy Rosser

(57) ABSTRACT

An endoscopic cleaning device capable of properly removing wet cerumen from an auditory canal while the interior of an auditory canal is illuminated. The device allows an image of the interior of the auditory canal to be acquired while the auditory canal is being cleaned. The device has an ear picking main body that also serves as a light guide to provide the illumination. The ear picking main body rotates about a light guide containing the micro lens used to acquire the image, so that the image remains stable. The ear picking main body is inserted through a removable, elastically deformable tubular ear picking part having a through hole and an outer layer made of fibrous material. In this way light can be delivered to the end of the ear picking main body, and the fibrous material of the ear picking part can be used to remove wet cerumen.

27 Claims, 12 Drawing Sheets

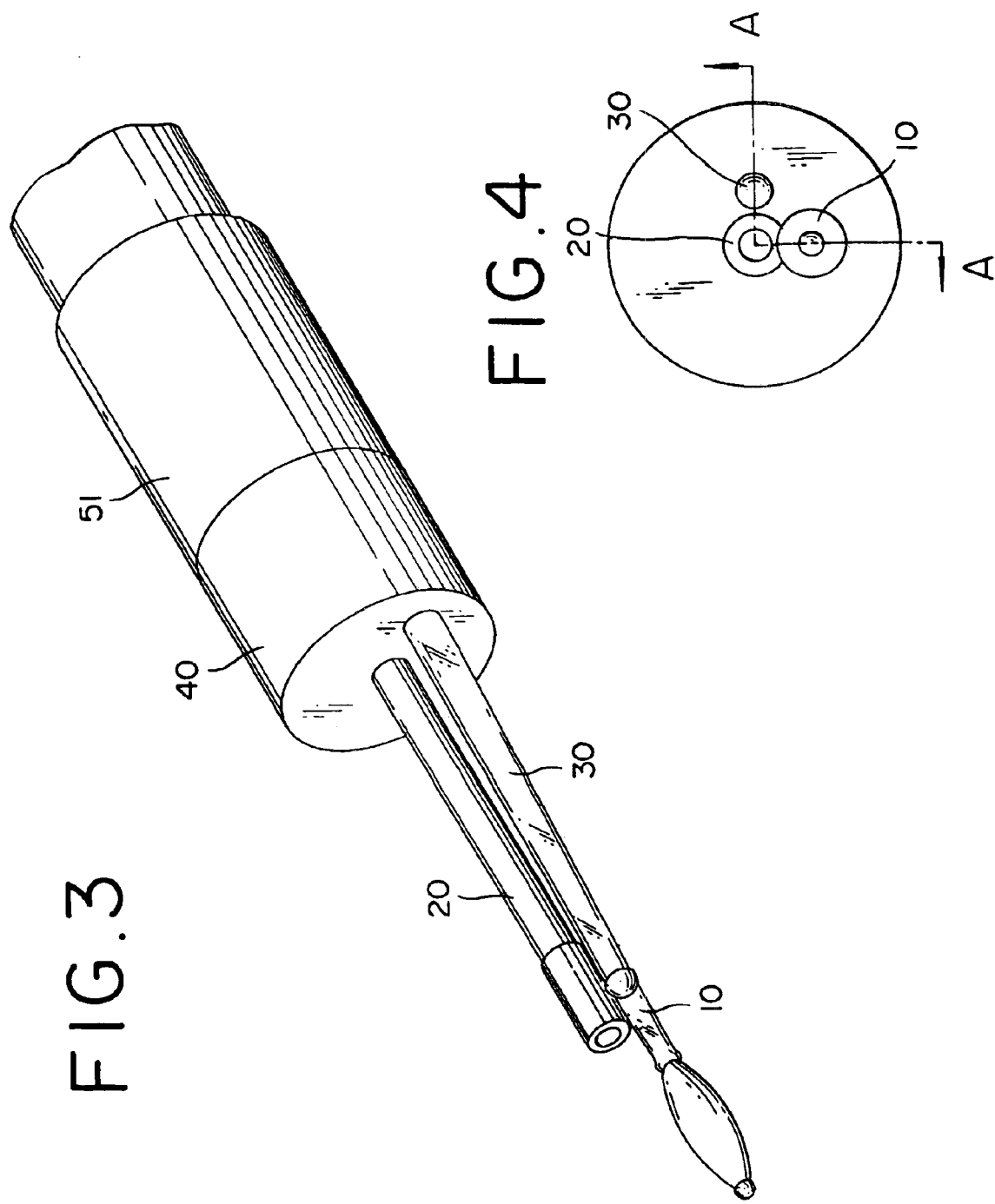

ENDOSCOPIC AUDITORY CANAL CLEANING APPARATUS

CROSS REFERENCE TO RELATED APPLICATIONS

This application is related to, and claims priority from Japanese Patent Application No. 2003-162942 filed on Jun. 6, 2003, the entire contents of which are hereby incorporated by reference.

BACKGROUND OF THE INVENTION

1. Field of the Invention

This invention relates to an endoscopic auditory canal cleaning apparatus which is capable of removing cerumen safely and infallibly.

2. Description of the Prior Art

Since no one can look into the interior of one's own auditory canal, the practice of cleaning the auditory canal by rummaging the interior of the auditory canal on the principle of trial and error has been in vogue to date. The act of rummaging the interior of the ear in strict accordance with intuition, however, cannot be trusted to attain removal of cerumen actually as expected and, on account of its possibility of inflicting injury to the interior of the auditory canal, cannot be regarded as safe.

As a solution for this problem, an endoscopic auditory canal cleaning apparatus which enables the user to clean the interior of the auditory canal while continuing his observation of the situation of the interior of the auditory canal (disclosed in Japanese Patent Publication No. 2001-204,647, for example) has been invented and already developed for practical use. This endoscopic auditory canal cleaning apparatus is furnished with a scraping part resembling a spoon in shape. The user of the apparatus is enabled to remove the cerumen safely and infallibly by the procedure of scooping the cerumen on the scraping part and carrying it as held thereon out of the auditory canal while keeping an eye on the situation of the interior of the auditory canal.

The human cerumen is discriminated between dry cerumen and wet cerumen. For the purpose of removing dry cerumen in cleaning a given ear, the scraping part of the shape of a spoon mentioned above proves excellent. When the cleaning is aimed at removing wet cerumen, however, the cerumen which is in a semiliquid or liquid state and is devoid of a constant form cannot be scooped very satisfactorily with the scraping part of the shape of a spoon. If the wet cerumen is scooped at all, it cannot be easily removed thoroughly because it partly survives the removal.

In the existing circumstance, therefore, the desirability of providing an endoscopic auditory canal cleaning apparatus which fulfills an excellent function of enabling the user to remove even wet cerumen while keeping an eye on the interior of the auditory canal has been finding popular recognition. Generally, for the purpose of removing wet cerumen, a cotton swab having a wad of cotton wound around the leading tip of a stick is used. The cotton swab is capable of entwining the wet cerumen about itself.

It should be noted here, however, that the cotton swab cannot be applied in its unaltered form to the endoscopic auditory canal cleaning apparatus disclosed in the aforementioned patent publication (Cited Reference 1). The reason for this unavailability of the cotton swab is that the endoscopic auditory canal cleaning apparatus disclosed in the Cited Reference 1 uses a scraping part of the shape of a spoon produced as a transparent body so constructed as to guide the light to the leading terminal thereof with a view to radiating the interior of the auditory canal fully satisfactorily with light. By merely replacing this scraping part with the cotton swab, it is not made possible to guide the light to the leading terminal of the cotton swab on which the cotton is wound.

SUMMARY OF THE INVENTION (1) An endoscopic auditory canal cleaning apparatus contemplated by this invention comprising:

a light source for generating light, an ear picking main body so formed as to guide the light generated by said light source to be guided to the leading terminal thereof, an ear picking part furnished with a surface layer made of a fibrous material adapted to be disposed in said ear picking main body by exposing said leading terminal, an image incorporating means for taking in an image of the interior of the auditory canal radiated by the light guided to the leading terminal of said ear picking main body, a display means for displaying the image incorporated by said image incorporating means, and a holding means furnished with a hollow mouth to be penetrated by said image incorporating means and allowed to rotate freely around said image incorporating means as the central axis with said ear picking main body kept in a held state.

According to the endoscopic auditory canal cleaning apparatus of this invention, the interior of the auditory canal can be radiated with the light emitted at the leading terminal of the ear picking main body and the image of the interior of the auditory canal can be incorporated by the image incorporating means. Here, the holding means for holding the ear picking main body can be freely rotated around the an image incorporating means as the central axis. It is, therefore, made possible to clean the interior of the auditory canal by freely rotating the ear picking main body alone while keeping the image fixed in one direction. Since the direction of the image is fixed, the interior of the auditory canal can be cleaned safely and infallibly without losing sight of the objective such as cerumen.

This invention particularly befits the removal of wet cerumen because the surface of the ear picking part disposed at the leading terminal of the ear picking main body is covered with a fibrous material and the ear picking part and the ear picking main body therefore fulfill the function of a cotton swab. Since the ear picking main body is so constructed as to guide the light to the leading terminal thereof, it can radiate the interior of the auditory canal brightly in spite of the fact that the leading terminal side of the ear picking main body is covered with the ear picking part. Consequently, it is made possible to acquire an image of the interior of the auditory canal.

(2) An another endoscopic auditory canal cleaning apparatus contemplated by this invention comprising:

a light source for generating light, a light guide for guiding the light generated by said light source to the leading terminal thereof and radiating the interior of the auditory canal, an ear picking main body shaped like a bar, an ear picking part disposed on the outer periphery of the leading terminal of said ear picking main body and furnished with a surface layer made of a fibrous material, an image incorporating means for incorporating an image of the interior of the auditory canal radiated by said light guide, a display means for displaying the image incorporated by said image incorporating means, and a holding means furnished with a hollow mouth to be penetrated by said image incorporating means and allowed to rotate freely around said image incorporating means as the central axis with said ear picking main body kept in a held state.

The endoscopic auditory canal cleaning apparatus contemplated by this invention, by having a light guide inserted therein, is enabled to radiate the interior of the auditory canal brightly and facilitate the acquisition of the image of the interior of the auditory canal. Since this apparatus is capable of brightly radiating the interior of the auditory canal in consequence of the irradiation of light through the medium of the light guide, it permits effective use therein of the commercially available opaque ear pick (cotton swab) of the type using a cotton winding which has been in popular use to date.

BRIEF DESCRIPTION OF THE DRAWINGS

FIG. 3 is a perspective view illustrating an ear pick fitting part and a first terminal part of a supporting tube.

FIG. 4 is a front view of the ear pick fitting part.

DETAILED DESCRIPTION OF THE INVENTION

Now, embodiments of this invention will be described in detail below with reference to diagrams attached hereto.
[First Embodiment]

Figure 1:
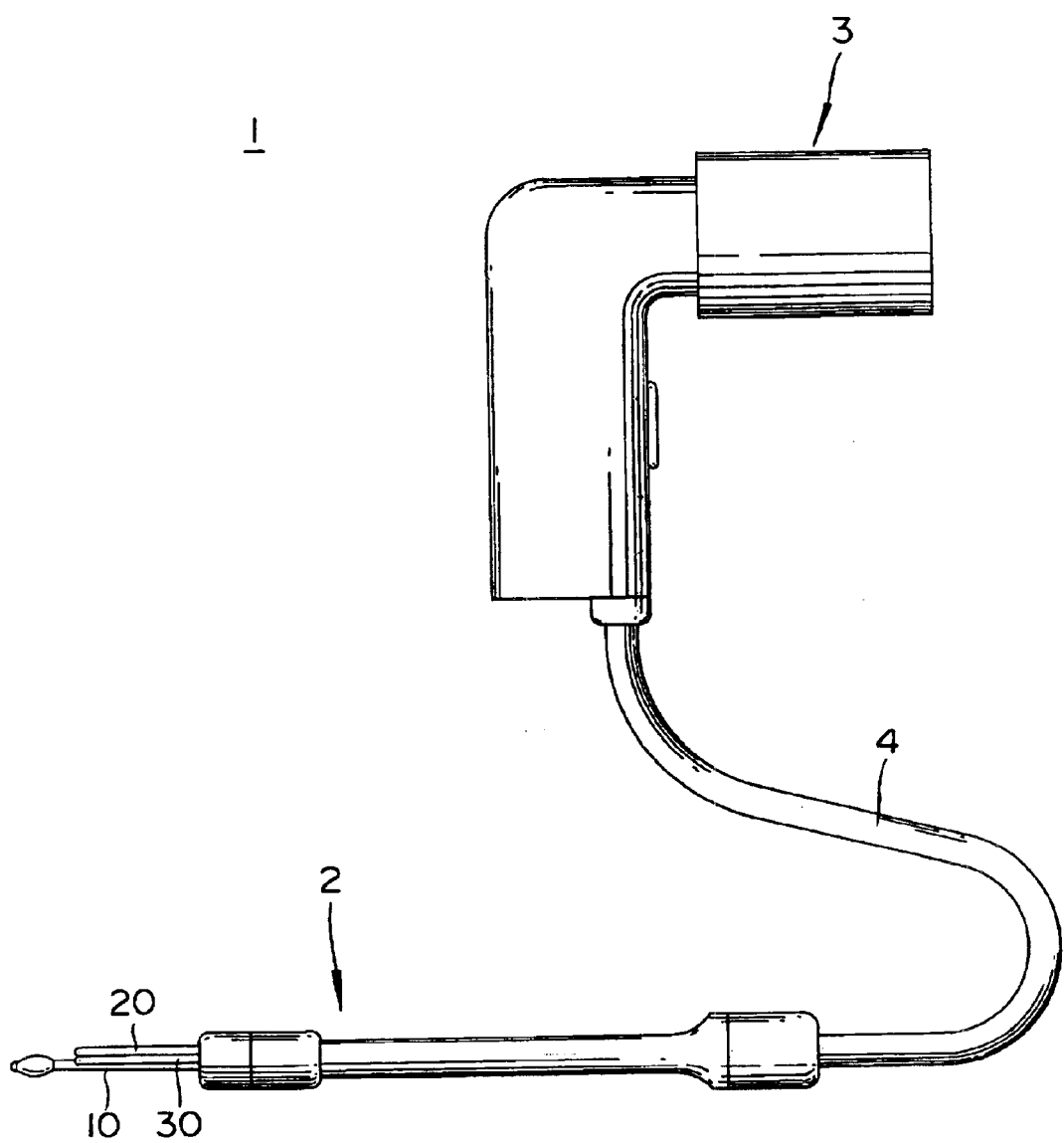
FIG. 1 is a general view of an endoscopic auditory canal cleaning apparatus according to an embodiment of this invention.

FIG. 1 is a general view of an endoscopic auditory canal cleaning apparatus according to an embodiment of the invention.

An endoscopic auditory canal cleaning apparatus 1 is composed of an ear picking device 2 and a display device (indicating means) 3. The ear picking device 2 and the display device 3 are interconnected by means of a protecting tube 4.

The ear picking device 2 is furnished with an ear picking main body 10 intended to irradiate the interior of the auditory canal and clean it as well, a fiber scope 20 (image injecting means) provided at the leading terminal thereof with an image micro lens and adapted to take in the image of the interior of the auditory canal through the image micro lens, and a light guide 30 adapted to irradiating the interior of the auditory canal.

The image which has been picked up with the image micro lens is transmitted by the fiber scope 20 in the protecting tube 4 and displayed as magnified by the display device 3.

Figure 2:
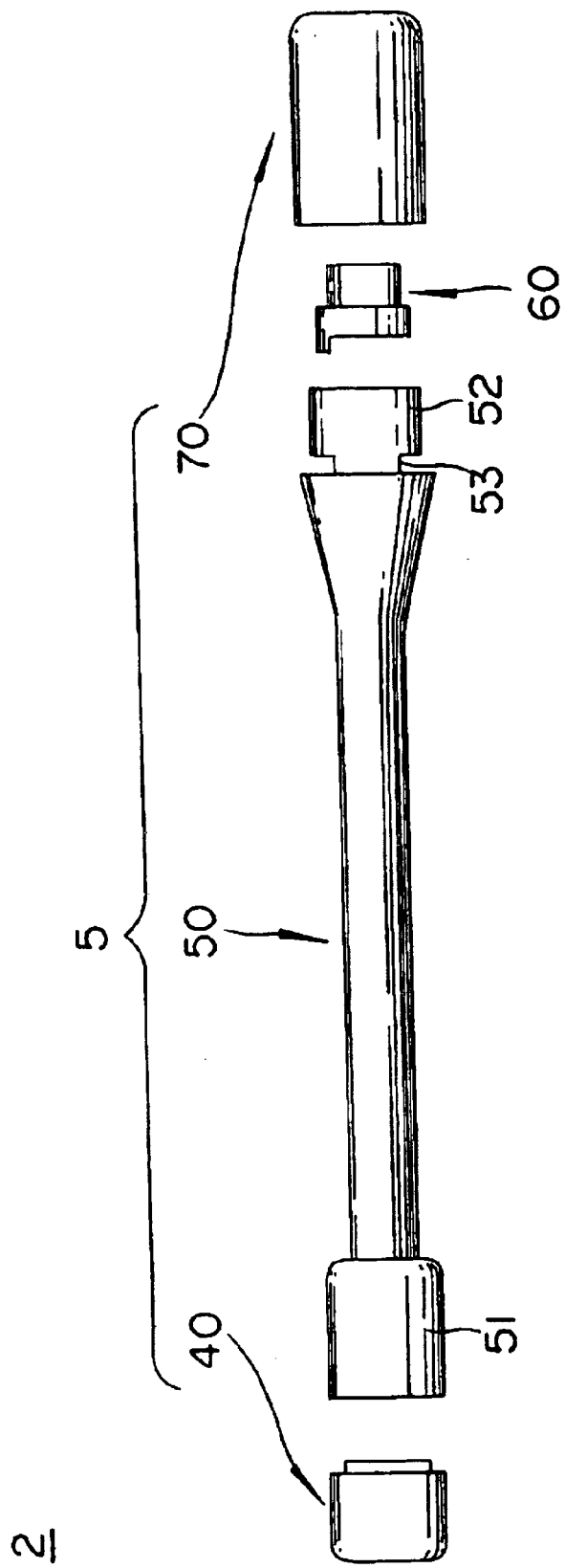
FIG. 2 is a diagram illustrating the construction of an ear picking device.

FIG. 2 is a diagram illustrating the construction of the ear picking device.

The ear picking device 2 is furnished with an ear pick mounting part 40, a supporting tube 50, an image guide fixing part 60, and a joining part 70 besides the ear picking main body 10, fiber scope 20, and light guide 30 which are mentioned above.

The ear pick mounting part 40 is joined to a first terminal part 51 of the supporting tube 50 by ultrasonic welding or screwing. A second terminal part 52 of the supporting tube 50 is furnished with a concave part 53 and is joined to the joining part 70 by establishing convexo-concave fitting between the convex part 53 and a hooking part formed on the inner surface of the joining part 70. Inside the second terminal part 52, the image guide fixing part 60 is disposed as opposed thereto across a slight gap. The supporting tube 50 is rotatable relative to the image guide fixing part 60.

The ear pick mounting part 40, supporting tube 50, and joining part 70 are joined in series to give rise to a holding part. (holding means) 5. The ear pick mounting part 40, supporting tube 50, and joining part 70 are severally formed in a hollow construction. Inside the holding part 5 which is formed by joining these hollow members, an inner empty space which will be specifically described afterward is formed.

The components of the ear picking device 2 will be described specifically below.

FIG. 3 is a perspective view depicting the ear pick mounting part and the first terminal part of the supporting tube and FIG. 4 is a front view of the ear pick mounting part.

The ear picking main body 10, fiber scope 20, and light guide 30, as illustrated in FIG. 3 and FIG. 4 are so disposed as to form angles each approximating 90 degrees and are made to extrude from the ear pick mounting part 40.

(Ear Picking Main Body 10)

For a start, the ear picking main body 10 will be described with reference to FIG. 5–FIG. 8.

Figure 5:
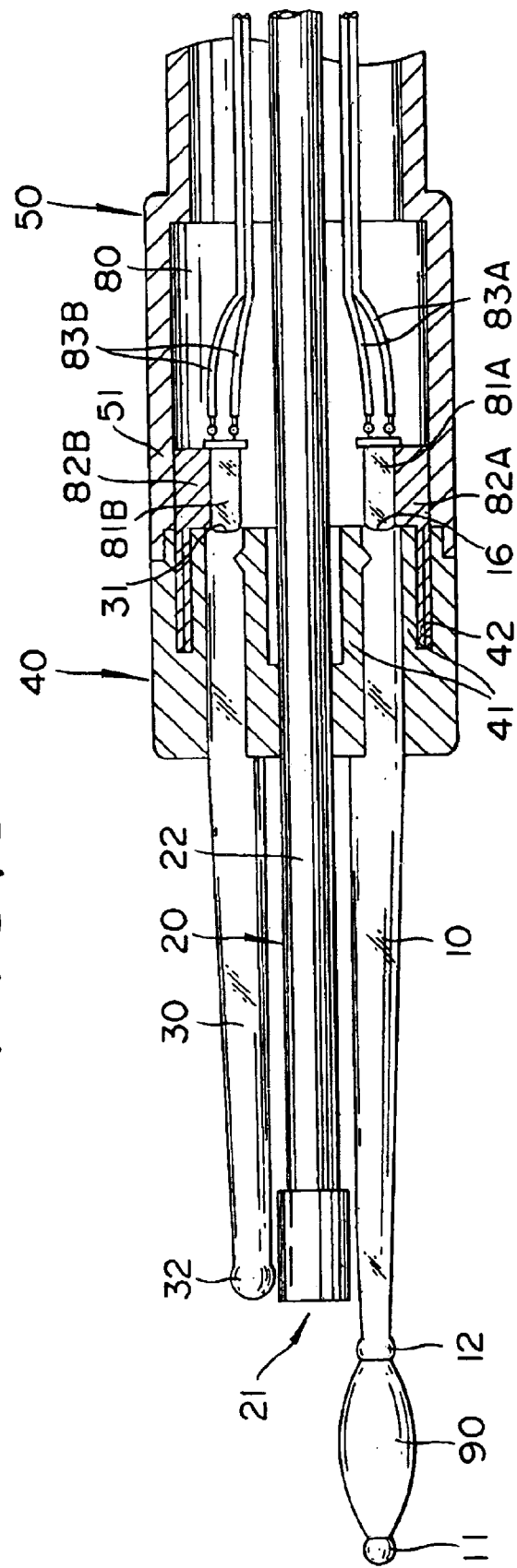
FIG. 5 is a cross section taken through FIG. 4 along the line A—A.
Figure 6:
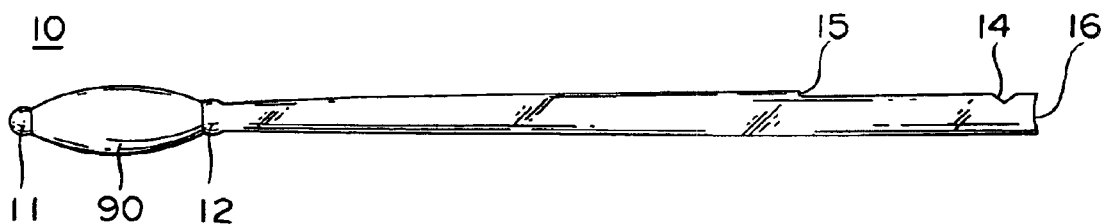
FIG. 6 is a diagram depicting the main body of the ear pick.
Figure 7:
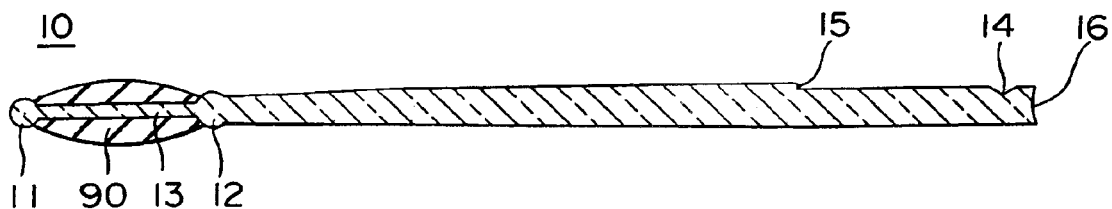
FIG. 7 is a cross section of the main body of the ear pick.
Figure 8:
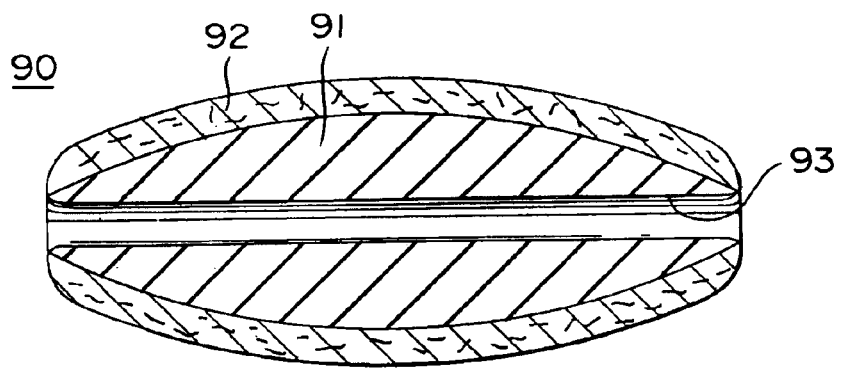
FIG. 8 is a magnified cross section of an ear picking part.

FIG. 5 is across section taken through FIG. 4 across the line A—A, FIG. 6 is a diagram depicting the ear picking main body, FIG. 7 is a cross section of the ear picking main body, and FIG. 8 is a magnified cross section of the ear picking part.

The ear picking main body 10 is formed of a transparent resin with a view to allowing the light received from a light source 81A to be transmitted as far as the leading terminal thereof as illustrated in FIG. 5–FIG. 7. The term "transparent resin" as used herein refers to a plastic formed of a raw material selected from among cycloolefin polymer, acrylic resin, polycarbonate, vinyl chloride resin, styrene resin, APO resin, and polymethyl methacrylate, for example. It is particularly proper to adopt the cycloolefin polymer as the raw material for the ear picking main body 10 because it enjoys low hygroscopicity and excels in translucency and heat resistance.

The ear picking main body 10 is provided at the leading terminal thereof with a first engaging part 11 and a second engaging part 12 which are arrayed in a longitudinal direction. The first engaging part 11 and the second engaging part 12, as illustrated in FIG. 7, are formed in larger diameters than an ear pick holding part 13 which intervenes therebetween. The light received is transmitted via the second engaging part 12 and the ear pick holding part 13 till the first engaging part 11 and then emitted therefrom.

The ear picking main body 10 has an ear picking part 90 attached thereto so as to expose the leading terminal thereof. The ear picking part 90 is interposed between the first engaging part 11 and the second engaging part 12 and attached to the periphery of the ear pick holding part 13.

The ear picking part 90 is composed, as illustrated in FIG. 8, of a base 91 and a fibrous part 92 (surface layer) held by the base 91 and adapted to cover it. The base 91 is formed of an elastic body such as of rubber or sponge. The fibrous part 92 is formed of a fibrous material such as of cotton. The fibrous part 92 is obtained by the adhesion of the fibrous material to the base 91 as with an adhesive agent. Alternatively, the fibrous part 92 may be obtained by the adhesion of the fibrous material to a cover serving to protect the base 91.

The base 91 has a through hole 93 formed therein. The through hole 93 is formed in a smaller diameter than the first engaging part 11 and second engaging part 12 of the ear picking main body 10. During the attachment of the ear picking part 90 to the ear picking main body 10, therefore, the first engaging part 11 of the ear picking main body 10 is inserted into the through hole 93 while the base 91 is kept elastically deformed. The base 91 resumes the original shape thereof at the position at which the first engaging part 11 has completely penetrated the through hole 93. At this point, the leading terminal side of the base 91 collides against the first engaging part 11 and the basal terminal side thereof collides against the second engaging part 12 respectively. The movement in the longitudinal direction, therefore, is restricted by the first engaging part 11 and the second engaging part 12. Incidentally, the leading terminal side and basal terminal side of the base 91 designate the same directions as the leading terminal side and basal terminal side of the ear picking main body 10.

With reference again to FIG. 5 and FIG. 6, the ear picking main body 10 has a concave part 14 formed in the basal terminal part thereof. The concave part 14 can be joined, in the pattern of convexo-concave union, to a pair of recessing members 41 formed inside the ear pick mounting part 40. In consequence of this union, the ear picking main body 10 is rendered removable relative to the ear pick mounting part 40. Since the ear picking main body 10 is replaceable by virtue of the removability thereof, it can be replaced with a new supply whenever it is polluted. This replacement ensures the cleaning apparatus to offer hygienic use constantly for the user.

The ear picking main body 10 is further provided in the basal terminal part thereof with a step 15. During the insertion of the ear pick mounting part 40, this step 15 prevents the ear picking main body 10 from excessively entering the ear pick mounting part 40 or an end face 16 from colliding against the light source 81A. Specifically, by the provision of the step 15, the insertion of the ear picking main body 10 is restricted at the position at which the end face 16 just collides against the light source 81A. The ear picking main body 10 receives the light from the light source 81A at the end face 16.

The ear picking main body 10 is formed as slanted more or less in the direction of the fiber scope 20 from the perpendicular line relative to the ear pick mounting part 40. Owing to this slant, the ear picking device 2 is converged toward the leading terminal thereof and the insertion of the ear picking device 2 into the auditory canal and the cleaning of the interior of the auditory canal are facilitated. The ear picking part 90 which is held by the ear picking main body 10 is disposed within the field of view which can be observed from the image micro lens 21 of the fiber scope 20. The ear picking main body 10, however, is slanted to an extent such that the ear picking part 90 may avoid concealing more than one half of the field of view of the fiber scope 20. Since the ear picking part 90 does not obstruct the field of view of the fiber scope 20, the necessary observation of the interior of the auditory canal and the safe cleaning of the interior of the auditory canal can be accomplished as expected.

(Fiber Scope 20)

Now, the fiber scope 20 will be described below with reference to FIG. 5 and FIG. 9.

Figure 9:
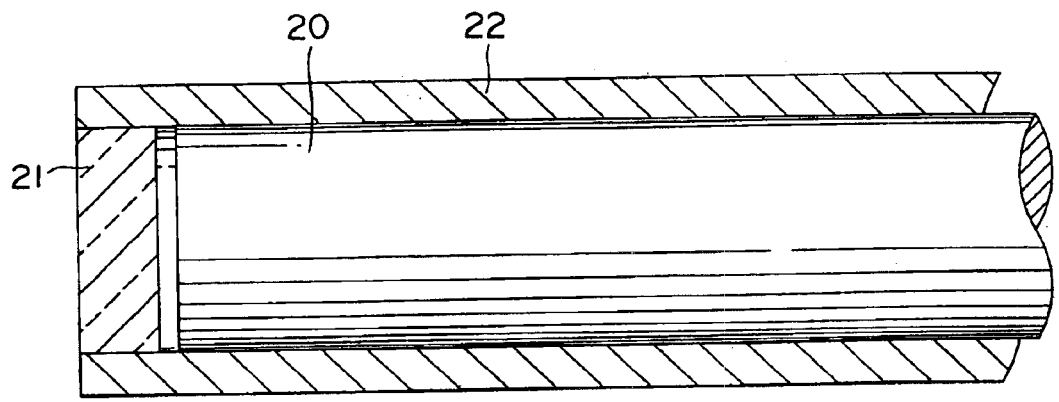
FIG. 9 is a cross section illustrating a fiberscope having an image micro lens mounted inside the leading terminal of a protecting pipe.

FIG. 9 is a cross section illustrating a fiber scope having an image micro lens attached to the interior at the leading terminal of a protecting pipe.

The fiber scope 20, as illustrated in FIG. 9, is provided at the leading terminal thereof with an image micro lens 21 (objective lens) which is intended as an image incorporating part to incorporate an image of the interior of the auditory canal. The fiber scope 20 excepting the part of the image micro lens 21 is covered with a protecting pipe 22 made of stainless steel. As a result, the fiber scope 20 is linearly fixed and is prevented from sustaining fracture and curvature. The fiber scope 20 which is linearly fixed penetrates the holding part 5. The image micro lens 21 is made to adhere integrally to the fiber scope 20 with an adhesive agent and is fixed by being clamped from outside the protecting pipe 22.

The length of the image micro lens 21 of the fiber scope 20 which protrudes from the ear pick mounting part 40 is preferred to be not less than one half of the length of the ear picking main body 10 which protrudes from the ear pick mounting part 40. So long as the extent of protrusion is roughly this much, the fiber scope 20 easily takes in an image of the neighborhood of the ear picking part 90. If the distance between the image micro lens 21 and the ear picking main body 10 is too small or too large, the incorporation of a clear image will become difficult.

To be specific, the image micro lens 21 is preferred to be disposed at a position separated by a distance in the range of 10 mm to 15 mm from the ear picking part 90. So long as the incorporation of an image of the interior of the auditory canal encounters no hindrance and the ear picking part 90 has room enough to avoid interfering with the removal of a foreign substance from the interior of the auditory canal, the length of the protrusion of the image micro lens 21 of the fiber scope 20 may be larger or smaller than one half of the length of the protrusion of the ear picking main body 10.

The fiber scope 20 is passed through the ear pick mounting part 40, the supporting tube 50, the image guide fixing part 60, the joining part 70, and the interior of the protecting tube 4 and eventually connected to the display device 3. Incidentally, the fiber scope 20 contains image fibers and transfers an image through the image fibers.

(Light Guide 30)

The light guide 30 will be described below with reference to FIG. 5.

The light guide 30 is formed of a transparent resin similarly to the ear picking main body 10 and is inserted removably to the ear pick mounting part 40 in the pattern of convexo-concave union. An end face 31 of the light guide 30 remains in contact with a light source 81B and receives the light emitted by the light source 81B. The received light is sent through the interior of the light guide 30 and emitted by an irradiating part 32 to radiate the interior of the auditory canal. The light guide 30 fulfills the role of assisting the ear picking main body 10 in radiating the interior of the auditory canal.

The amount of protrusion of the irradiating part 32 of the light guide 30 from the ear pick mounting part 40 (holding part 5) is roughly the same as the amount of protrusion of the image micro lens 21 of the fiber scope 20. Owing to this approximate equality of the protrusion, the interior of the auditory canal can be brightly radiated without interfering with the field of view of the image micro lens 21 of the fiber scope 20.

The light guide 30 has the same construction as the ear picking main body 10 and can be removably attached to the holding part 5 in the pattern of convexo-concave union. The light guide 30 and the ear picking main body 10, therefore, can exchange their positions.

(Ear Pick Mounting Part 40 and Supporting Tube 50)

Figure 10:
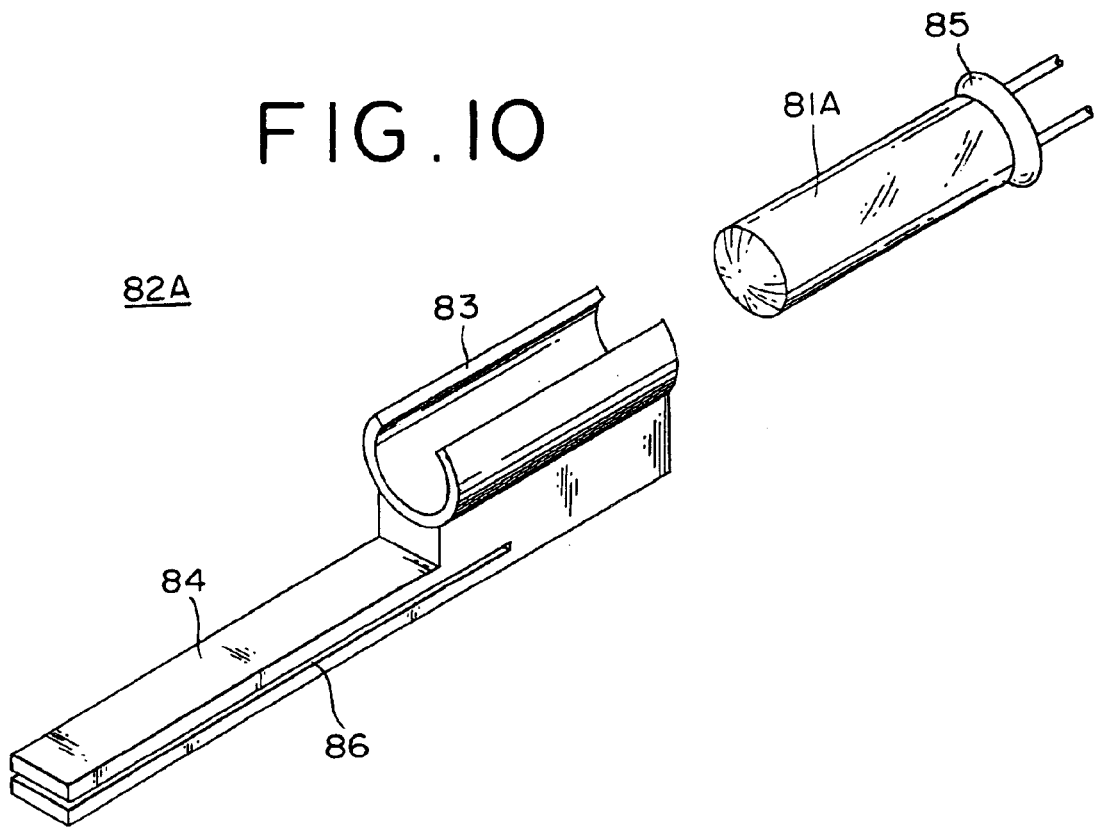
FIG. 10 is a perspective view of a light source holder.

The ear pick mounting part 40 and the supporting tube 50 will be described below with reference to FIG. 5 and FIG. 10. FIG. 10 is a perspective view of a light source holder.

The ear pick mounting part 40 and the supporting tube 50 are both formed in hollow constructions. The ear pick mounting part 40 and the supporting tube 50 jointly form part of an internal empty space 80 in the holding part 5. In the internal empty space 80, the fiber scope 20 and the light sources 81A, B serving to emit the light for radiating the interior of the auditory canal are disposed.

The light sources 81A, B are light emitting diodes (LED), incandescent lamps, or the like, for example. The light source 81A is retained by a light source holder 82A and is so positioned as to confront the end face 16 of the ear picking main body 10. The light source 81B is retained by a light source holder 82B and is so positioned as to confront the end face 31 of the light guide 30.

The light source holder 82A, as illustrated in FIG. 10, is furnished with a light source holder 83 for holding the light source 81A and an embedding part 84 destined to be inserted into the ear pick mounting part 40. The light source holding part 83 has the inside perimeter thereof formed in a shape resulting from notching part of a cylinder conforming with the light source 81A. The light source 81A is inserted into the light source holding part 83 from behind till a terminal part 85 of the light source 81A collides against the light holding part 83.

The embedding part 84 is inserted into a concave part 42 which is set up in the ear pick mounting part 40. The embedding part 84 has a slit 86 formed therein. When the embedding part 84 is somewhat smaller than the concave part 42, therefore, the embedding part 84 and the concave part 42 are made to conform with each other by decreasing the gap of the slit 86. When the gap of the slit 86 is decreased, the embedding part 84 is fixed firmly to the concave part 42 because the gap is urged by this decrease to resume the former size.

The light source 81B is likewise fixed and positioned by the light source holder 82B.

Optionally, the light source 81A may be attached to the light source holder 82A after the light source holder 82A has been inserted into the ear pick mounting part 40. Conversely, the light source holder 82A may be attached to the ear pick mounting part 40 after the light source 81A has been attached to the light source holder 82A.

To the light sources 81A, B, the electric power from the display device 3 is supplied respectively via two conductors 83A, B. The light sources 81A, B are each caused by the received electric power to emit light and radiate the end face 16 of the ear picking main body 10 and the end face 31 of the light guide 30. Since the light sources 81A, B directly radiate the ear picking main body 10 and the light guide 30, they are capable of supplying intense light. The conductors 83A, B are extended to the display device 3.

(Image Guide Fixing Part 60 and Protecting Tube 4)

The appearance of the connection of the image guide fixing part 60 and the protecting tube 4 will be explained below with reference to FIG. 11 and FIG. 12.

Figure 11:
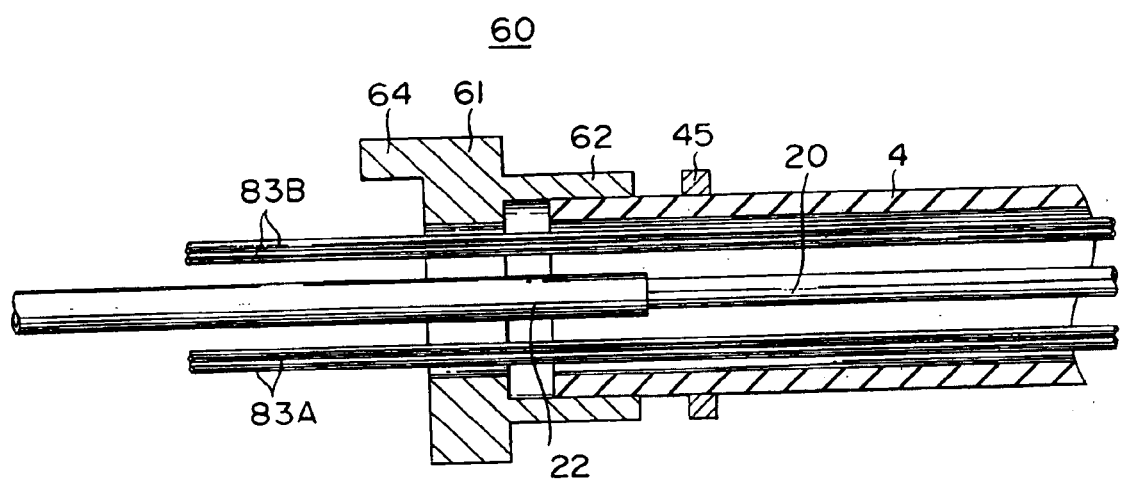
FIG. 11 is a cross section illustrating an image guide fixing part and a protecting tube.
Figure 12:
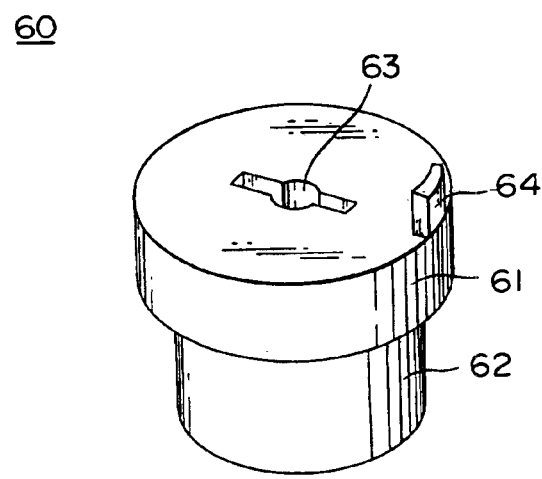
FIG. 12 is a perspective view of the image guide fixing part.

FIG. 11 is a cross section of the image guide fixing part and the protecting tube and FIG. 12 is a perspective view of the image guide fixing part.

The image guide 60 is furnished with a fixing part main body 61 and a protecting tube mounting part 62.

The fixing part main body 61 holds the conductors 83A, B and the fiber scope 20 which is covered with the protecting pipe 22. The fixing body main body 61, therefore, has formed therein a hole 63 which is penetrated by the protecting pipe 22 and the two conductors 83A, B. The hole 63, as illustrated in FIG. 12, is furnished with apart allowing insertion of the protecting pipe 22 and parts allowing passage of the conductors 83A, B. The protecting pipe 22 is inserted through the hole 63 and fixed as with an adhesive material. The fixing part main body 61 has a projecting part 64 formed at a part thereof.

The protecting tube mounting part 62 allows insertion therein of the protecting tube 4 which has an annular snap 45 fixed on the outer periphery. The snap 45 is interposed between the joining part 70 illustrated in FIG. 2 and the image guide fixing part 60 and is fixed to the projecting tube 4. In the interval from the image guide fixing part 60 to the display device 3, the fiber scope 20 is not protected by the protecting pipe 22 but is protected by the protecting tube 4 instead. The fiber scope 20 and the conductors 83A, B are allowed to bend to the extent of being saved by the protecting tube 4 from sustaining fracture and disconnection respectively.

(Supporting Tube 50, Image Guide Fixing Part 60, and Joining Part 70)

Figure 13:
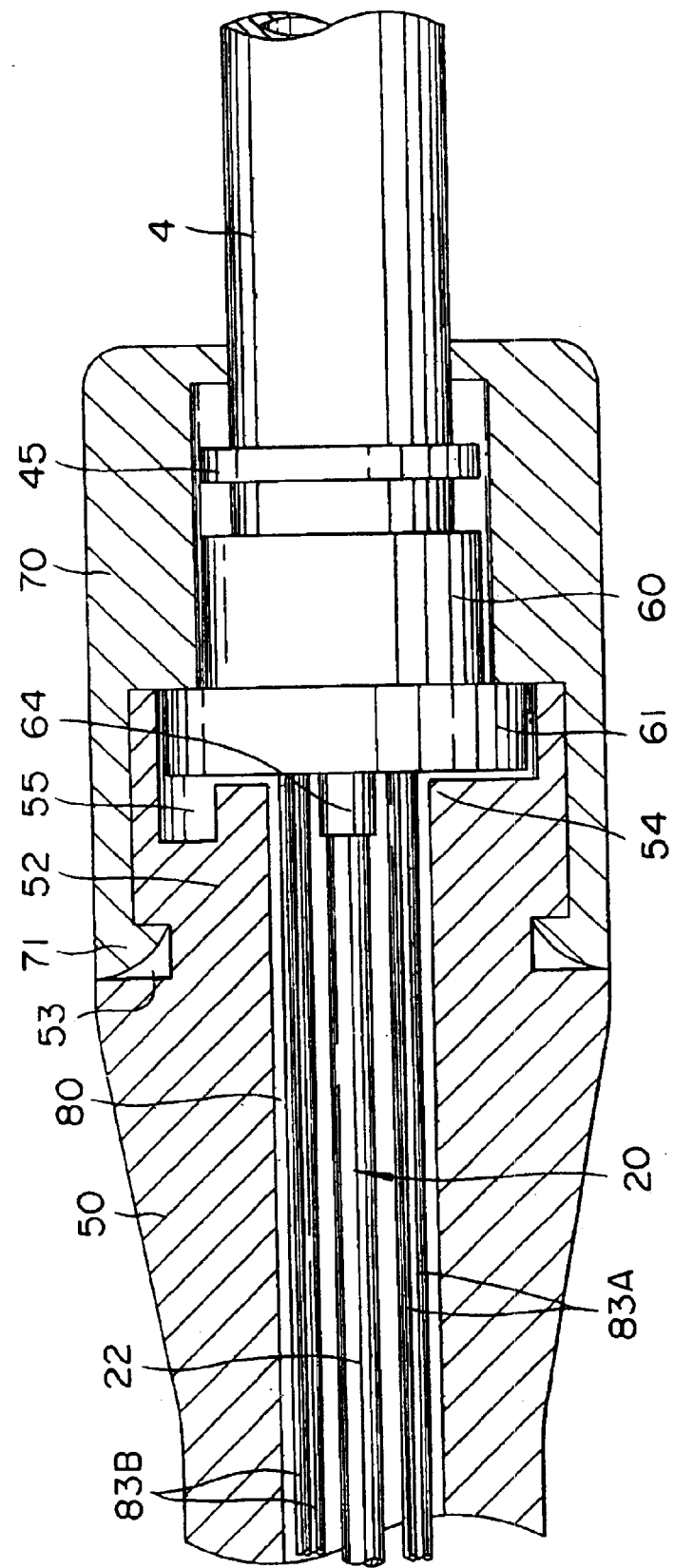
FIG. 13 is a cross section illustrating the state of combination of a supporting tube, an image guide fixing part, and a binding part.

FIG. 13 is a cross section illustrating the supporting tube 50, the image guide fixing part 60, and the joining part 70 in their combined state.

First, the protecting tube 4 which has the fiber scope 20 and the conductors 83A, B passed therein is inserted into the image guide fixing part 60. Here, the fiber scope 20 is inserted into the protecting pipe 22 and is passed together with the conductors 83A, B through the hole 63 formed in the image guide fixing part 60 (FIG. 12 refers). Then, through the medium of a slight gap, the fixing part main body 61 of the image guide fixing part 60 is inserted into the supporting tube 50.

The joining part 70 is furnished with a hooking part 71 which is intended to be inserted in the pattern of convexo-concave union into the concave part 53 (FIG. 2 refers) formed in the second terminal part 52 of the supporting tube 50. The joining part 70 which has been recessed in the supporting tube 50 encloses part of the protecting tube 4 and the image guide fixing part 60 therewith. Inside the joining part 70, the snap 45 is fixed on the outer periphery of the protecting tube 4. The protecting tube 4 cannot come off the joining part 70 because the snap 45 is confined in the joining part 70 and prevented from departing outward therefrom.

The supporting tube 50 and the joining part 70 are joined into a one-piece body by the convexo-concave union. A slight gap is interposed between the supporting tube 50 and the image guide fixing part 60. The supporting tube 50 and the joining part 70, therefore, are mutually rotatable relative to the image guide fixing part 60. The image guide fixing part 60 itself does not rotate, however, because the protecting pipe 22 is fixed to the image guide fixing part 60 and the fiber scope 20 incapable of rotation is fixed to the inner surface of the protecting pipe 22. That is, the supporting tube 50 and the joining part 70 are rotatable around the image guide fixing part 60 as the axis of rotation.

The two conductors 83A, B which protrude from the hole 63 of the image guide fixing part 60, as illustrated in FIG. 5, are connected to the light sources 81A, B. The light sources 81A, B rotate jointly with the supporting tube 50 because they have their positions fixed inside the first terminal part 51 of the supporting tube 50. The conductors 83A, B, therefore, are rotated on the light sources 81A, B sides and fixed on the first terminal part 51 side. If the supporting tube 50 is rotated in this state, the conductors 83A, B will twist and eventually sustain fracture and disconnection, depending on the number of rotations. With a view to precluding this hardship, an engaging mechanism capable of restricting the rotation of the supporting tube 50 is interposed between the image guide fixing part 60 and the supporting tube 50.

This engaging mechanism relies on the mutual intervention of a projecting part 64 of the image guide fixing part 60 and a lug 54 formed on the supporting tube 50 to prevent the supporting tube 50 from producing more than one rotation. The lug 54 is so formed as to contact the projecting part 64 before the supporting tube 50 completes one rotation of itself around the image guide fixing part 60 as the axis of rotation. The lug 54 is formed in part of an annular empty space 55 which is produced by cutting out the inner part of the second terminal part 52. Consequently, the empty space 55 disposed in the lug 54 assumes the shape of the letter C.

(Display Device 3)

Now, the construction of the display device 3 will be specifically described below with reference to FIG. 14.

Figure 14:
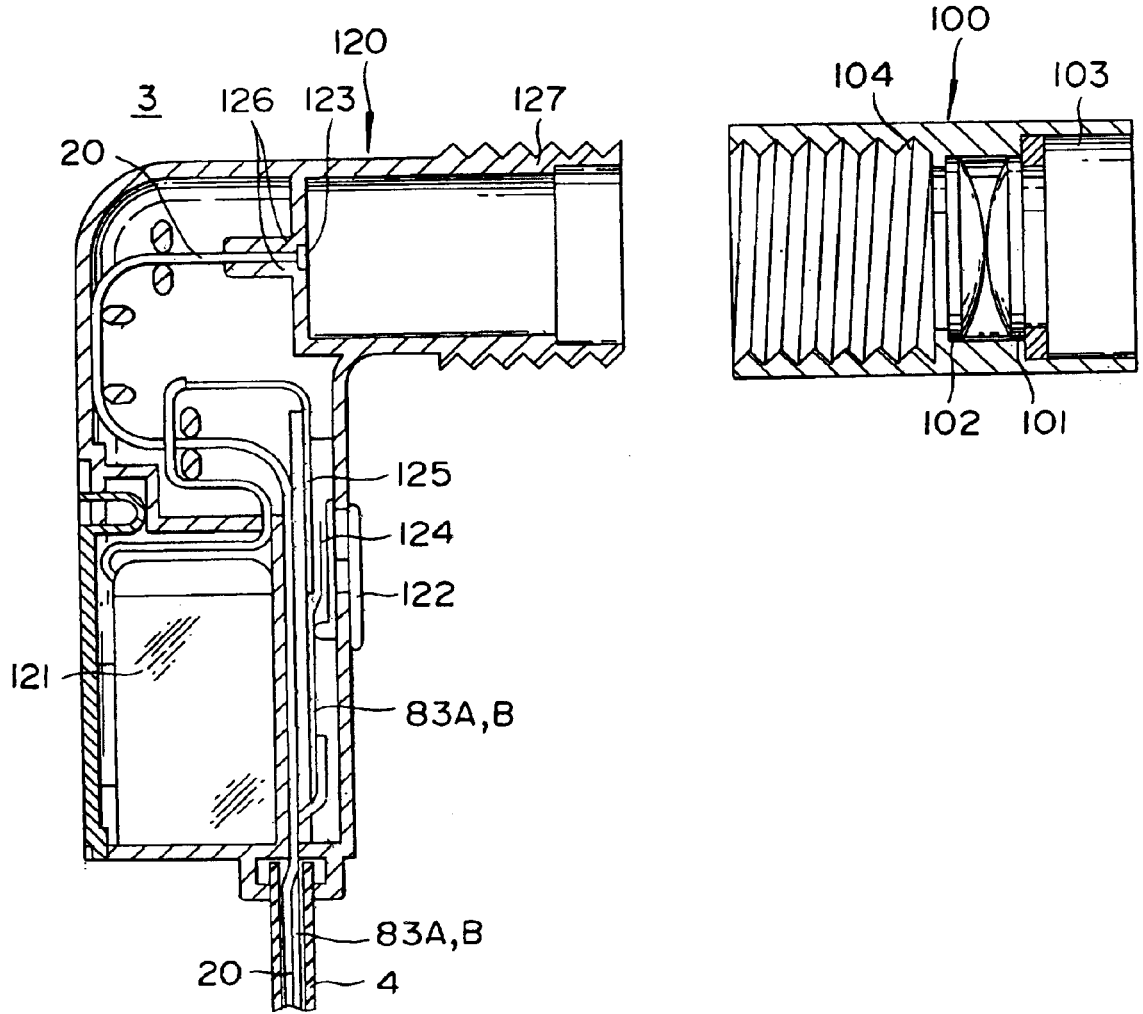
FIG. 14 is a cross section of a display device.

FIG. 14 is a cross section of the display device.

The display device 3 is furnished with an eyepiece part 100 and a display main body 120.

The eyepiece part 100 is provided with two planoconvex lenses 101 and 102. The planoconvex lens 101 is such that when the user needs to look at an image of the interior of the auditory canal, he is enabled to look into the planoconcave lens 101 from the plane side thereof through the medium of a shade 103. The shade 103 forms a shade around the planoconvex lens 101 to darken the affected area and render the image of the interior of the auditory canal reflected on the planoconvex lens 101 easy to observe. The planoconvex lens 102 is so disposed that the convex side thereof is opposed to the planoconvex lens 101 across a minute gap. In the eyepiece part 100, a threaded hole 104 is formed on the plane side of the planoconvex lens 102.

A display main body 120 is furnished with a battery 121 for supplying electric power to the light source 81, a switch 122 for interconnecting the battery 121 and the light source 81, and an aspherical lens 123 for magnifying an image transmitted by the fiber scope 20. When the switch 122 is slid (turned on) and the conductors 83A, B are connected via a fitting 124 to a conductor 125, the battery 121 supplies electric power to the light source 81. The aspherical lens 123 is disposed in the neighborhood of the end face of the fiber scope 20 which extends from the ear picking device 2 through the protecting tube 4. Incidentally, the end face of the fiber scope 20 and the aspherical lens 123 have their positions fixed by a wall part 126 formed on the inner wall of the display main body 120.

The display main body 120 is furnished with a screw part 127 which is helically inserted into the screw hole 104.

The eyepiece part 100 and the display main body 120 are combined into one body when the screw part 127 and the screw hole 104 are helically joined. The distance between the aspherical lens 123 and the planoconvex lens 102 can be adjusted by controlling the proportion of the helical insertion of the screw part 127. Even when the distance between the lenses in the display device 3 is delicately varied as by the change in temperature and the focal points of these lenses fail to coincide, therefore, necessary corrections can be easily made manually.

Now, the operation of the endoscopic auditory canal cleaning apparatus 1 will be explained below.

First, the user of the endoscopic auditory canal cleaning apparatus 1 turns on the switch 122 of the display device 3 and inserts the ear picking main body 10 of the ear picking device 2, the fiber scope 20 provided at the leading terminal thereof with the image micro lens 21, and the light guide 30 into his ear.

While the switch 122 remains in the ON state, the battery 121 supplies electric power to the light sources 81A, B via the conductors 83A, B. Consequently, the light sources 81A and 81B emit light and radiate the end face 16 of the ear picking main body 10 and the end face 31 of the light guide 30. The beams of light radiating the end faces are transmitted respectively through the ear picking main body 10 and the light guide 30 and made to emit light at the first engaging part 11 of the ear picking main body 10 and the radiating part 32 of the light guide 30 and radiate the interior of the auditory canal.

The fiberscope 20 introduces an image of the radiated interior of the auditory canal via the image micro lens 21. The image so introduced is transmitted via the fiber scope 20 to the display device 3 and magnified by the aspherical lens 123 within the display device 3. The magnified image is displayed on the planoconvex lens 101 via the planoconvex lens 102. Since the display device 3 magnifies the image of the interior of the auditory canal and renders it easy to observe, the user is enabled to clean the interior of the auditory canal easily.

The user removes the cerumen as he continues his observation of the interior of the auditory canal. Since the ear picking part 90 is made by the fibrous part 92 to function like a cotton swab, it can remove even a wet cerumen such as liquid or semiliquid cerumen by entwining it thereon. When the image of the interior of the auditory canal is blurred, the distance between the aspherical lens 123 and the planoconvex lens 102 can be adjusted and the focal points of the lenses can be aligned by rotating the eyepiece part 100 and changing the amount of the insertion of the screw part 127 into the screw hole 104.

The user manipulates the ear picking device 2 while taking hold of part of the holding part 5 of the ear picking device 2. This holding part 5 is rotatable around the image guide fixing part 60 as the axis of rotation. Since the fiber scope 20 which extends from the image guide fixing part 60 and the image micro lens 123 forming the leading terminal of the fiber scope 20 do not rotate, the image taken in through the fiber scope 20 remains in one fixed direction constantly. In contrast, the ear picking main body 10 which is attached to the ear pick mounting part 40 is rotatable about the fiber scope 20 as the axis of rotation. The apparatus is greatly safe and convenient because it enables the user to clean the interior of the auditory canal by properly rotating the ear picking main body 10 while continuing his observation of the image which is fixed in one direction constantly.

Further, since the engaging mechanism for restriction of rotation is interposed between the image guide fixing part 60 and the holding part 5, the possibility that the conductors 83A, B connected to the light source 81 in the ear pick mounting part 40 will twist unduly and sustain fracture in the inner empty space 80 of the holding part 5 is completely avoided.

The user, after completing the cleaning of the interior of the auditory canal, can extract the ear picking part 90 from the ear picking main body 10 and replace the used ear picking part 90 with a new supply to prepare the apparatus for next use. When the fibrous part 92 of the ear picking part 90 happens to be of the type merely covering the base 91, the apparatus can be prepared for next use by merely replacing the used fibrous part 92 with a new supply.

In the embodiment cited above, the ear picking main body 10 has been depicted as relying on the ear pick holding part 13 intervening between the first engaging part 11 and the second engaging part 12 to hold the ear picking part 90. This ear pick holding part 13 may be modified as illustrated in FIG. 15.

Figure 15:
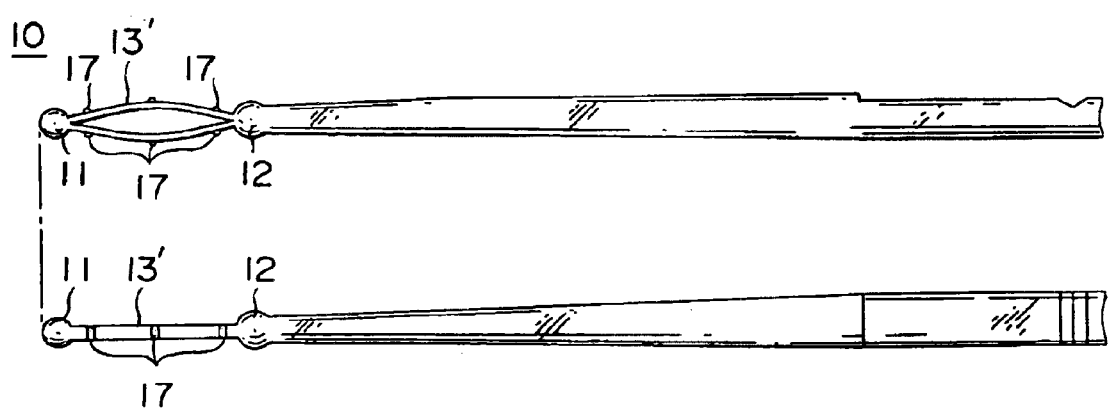
FIG. 15 is a diagram illustrating a modified example of a ear pick holding part in the main body of an ear pick.

FIG. 15 is a diagram illustrating a modified example of the ear pick holding part of the ear picking main body.

In an ear picking main body 10' illustrated in FIG. 15, an ear pick holding part 13' is so formed as to be branched provisionally into two portions at the second engaging part 12 and joined again into one body at the first engaging part 11. Owing to this shape, the ear holding part 13' fulfills the role of a leaf spring. Then, the ear pick holding part 13' as an energizing member energizes the base 91 with the force directed toward enlarging the through hole 93 during the attachment of the ear picking part 90. The ear picking part 90, because the base 91 is so energized, is strongly held by the ear pick holding part 13'. The ear pick holding part 13' is further furnished with engaging projections 17. The engaging projections 17 get caught in the through hole 93 of the ear picking part6 90 and prevent the ear picking part 90 from slipping in the longitudinal direction.

In the embodiment cited above, the ear pick mounting part 40 has the ear picking main body 10 attached thereto. This ear picking main body 10 is of the cotton-wound type having attached thereto the ear picking part 90 covered with the fibrous part 92. The ear picking main body 10 that is applicable to the endoscopic auditory canal cleaning apparatus 1 of this invention does not need to be limited to the cotton-wound type. Since the ear picking main body 10 is removable, it can be detached from the apparatus and replaced with an equivalent of other type.

Figure 16:
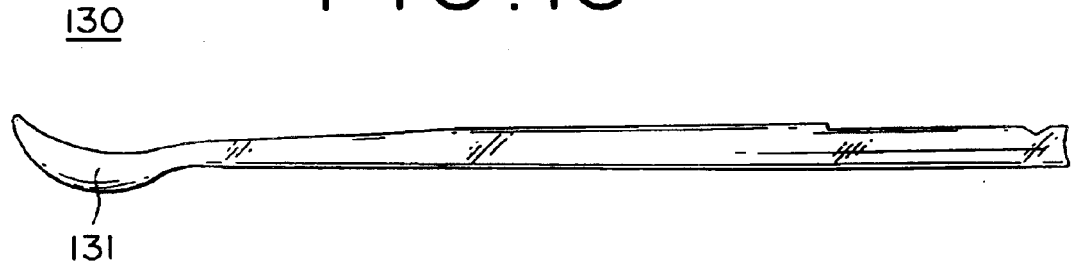
FIG. 16 is a diagram illustrating another example of the main body of an ear pick.
Figure 17:
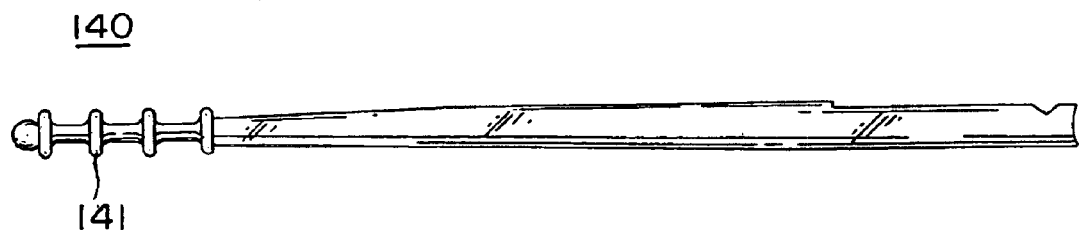
FIG. 17 is a diagram illustrating yet another example of the main body of the ear pick.

FIG. 16 is a diagram illustrating another example of the ear picking main body and FIG. 17 is a diagram illustrating yet another example of the ear picking main body.

For example, a spoon type ear picking main body 130 which is provided at the leading terminal thereof with a scraping part 131 of the shape of a spoon and adapted to guide light to the leading terminal as illustrated in FIG. 16 is available for the replacement. An annular ear picking main body 140 which is provided at the leading terminal thereof with a plurality of annular scraping parts 141 and adapted to guide light to the leading terminal as illustrated in FIG. 17 is otherwise available for the replacement. Further, a spiral type ear picking main body which, though not illustrated, is provided at the leading terminal thereof with a spring and adapted to guide light to the leading terminal is available for the replacement.

These spoon-type ear picking main body 130, annular type ear picking main body 140, and spiral type ear picking main body are invariably formed of transparent resin so that the light from the light source 81A or the light source 81B may be guided to the leading terminals. By interchanging such numerous ear picking main bodies to suit varying kinds of use, the user is enabled to clean the interior of the ear comfortably. The cotton-wound type ear picking main body 10 having the ear picking part 90 can be used for removing wet cerumen and the spoon-type ear picking main body 10 can be used for removing dry cerumen, for example.

Further, in the place of the ear picking main body made of a transparent resin, an ear pick formed of an opaque material may be used. For example, the ear pick mounting part 40 to which the conventionally used cotton-wound type ear pick, i.e. the cotton swab, is attached may be used. In this case, though the light for radiating the interior of the auditory canal is not emitted from the leading terminal of the cotton swab, the interior of the auditory canal can be cleaned satisfactorily by additionally using the light guide 30 and relying thereon to radiate the interior of the auditory canal brightly.

In the embodiment cited above, only one light guide 30 is mounted removably to the ear pick mounting part 40 in the pattern of convexo-concave union. The number of light guide 30 does not need to be limited to one. In order to reinforce the radiation of the interior of the auditory canal with light, two or more light guides 30 may be inserted in the ear pick mounting part 40. In this case, the use of these light guides 30 necessitates provision of as many light sources 81B.

In the embodiment cited above, the fiber scope 20 is depicted as being provided at the leading terminal thereof with the image micro lens 21. This provision, however, does not need to be construed as an exclusive specification. The fiber scope 20 may be provided at the leading terminal thereof with such a cover as illustrated in FIG. 18, for example.

Figure 18:
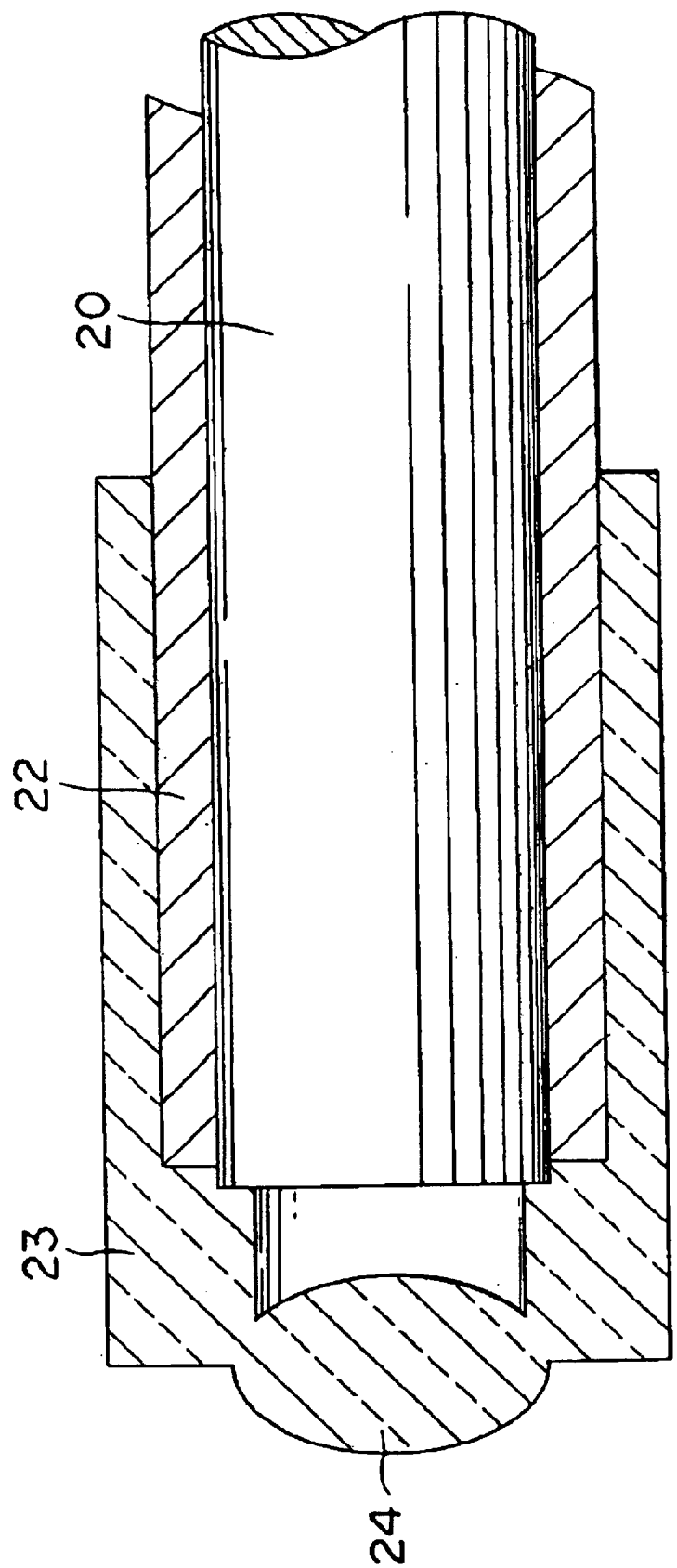
FIG. 18 is a cross section illustrating a cover for the fiber scope.

FIG. 18 is a cross section illustrating the cover for the fiber scope.

A cover 23 is integrally formed with the image micro lens 24 (object lens). Even when the field of view of the image micro lens 24 is deteriorated as with pollution or contamination owing to the repeated use of the endoscopic auditory canal cleaning apparatus 1, therefore, the image micro lens 24 can be easily replaced by changing the cover 23. In other words, the use of the cover 23 is at an advantage in enabling the clouded image micro lens to be replaced very easily without entailing the trouble of attaching the image micro lens to the leading terminal of the fiber scope 20.

The image micro lens 24 used herein is embraced by the cover 23 so that it may be disposed at the leading terminal of the fiber scope 20. The image micro lens 24, however, may be so embraced by the cover 23 as to be disposed in the proximity of the leading terminal of the fiber scope 20 or on the lateral surface thereof. Optionally, a prism may be used in the place of the image micro lens 24. While FIG. 18 depicts the integral formation of the cover 23 and the image micro lens 24 with one and the same material, it is permissible to have the cover 23 and the image micro lens 24 formed as separate bodies differing in material.

Further, the embodiment cited above has portrayed the case of using the fiber scope 20 which is provided at the leading terminal thereof with the image micro lens 21 as an image incorporating means. It is permissible, however, to use as an image incorporating means such a pickup element as the CCD camera. In this case, the display device is not furnished with such an image magnifying member as an aspherical lens or a planoconvex lens but is furnished instead with a device which is capable of subjecting a signal from the CCD camera to image processing and consequently forming an image.

The embodiment cited above has been described as utilizing the light source 81A and the light source 81B for directly radiating the ear picking main body 10 and the light guide 30. This utilization of the light sources, however, does not need to be construed as an exclusive specification. Optionally, convex lenses may be interposed severally between the light source 81A and the light source 81B and between the ear picking main body 10 and the light guide 30 and utilized for condensing the beams of light from the light sources 81A, B and supplying the condensed beams of light to the ear picking main body 10 and the light guide 30.

In the embodiment cited above, the ear picking main body 10, the fiber scope 20 (image micro lens 21), and the light guides 30 are disposed so as to form angles of about 90 degrees. Owing to this disposition of the relevant components, the areas required for disposing the ear picking main body 10, the fiber scope 20, and the light guide 30 can be decreased and the insertion thereof into the auditory canal can be facilitated. Here, in the embodiment cited above, the ear picking main body 10, the fiber scope 20, and the light guide 30 may be so disposed to form angles other than 90 degrees. They may be disposed to form any angles so long as their disposition does not interfere with the insertion thereof into the auditory canal.

[Second Embodiment]

In the first embodiment cited above, the ear picking main body 10 is removably attached to the ear pick mounting part 40 in the pattern of convexo-concave union. Owing to the union in this convexo-concave pattern, the ear picking main body 10 cannot rotate in itself. During the cleaning of the interior of the auditory canal, therefore, the same portions, particularly outside portions, of the fibrous part 92 of the ear picking part 90 are used frequently. Since the portions which are used frequently get dirty early, the intervals for replacing the ear picking part 90 become proportionately short. Notwithstanding this fact, the inside portions of the ear picking part 90 remain nearly undefiled. The ear picking part 90, therefore, proves uneconomical in the respect that it cannot be wholly used evenly and it is therefore inevitably replaced totally owing to the extreme defilement possibly sustained partly.

The second embodiment, with a view to overcoming the problem encountered by the first embodiment cited above, contemplates allowing the ear picking main body 10 to rotate in itself and consequently enabling the ear picking part 90 to be wholly used evenly. The second embodiment, thus, strives to ensue effective utilization of the whole of the ear picking part 90.

Now, the construction for rotating the ear picking main body 10 itself will be described below with reference to FIG. 19.

Figure 19:
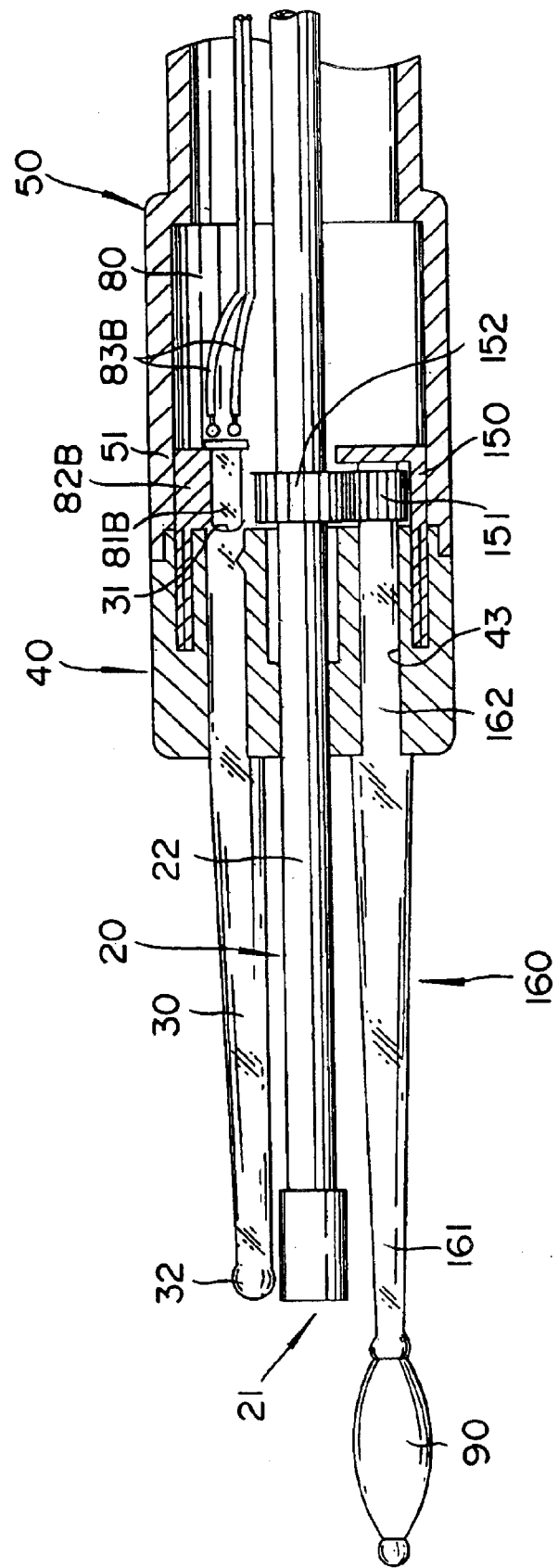
FIG. 19 is a cross section of the leading terminal of the ear picking device.

FIG. 19 is a cross section of the leading terminal of the ear picking device. The endoscopic auditory canal cleaning apparatus in the second embodiment has substantially the same construction as the endoscopic auditory canal cleaning apparatus 1 of the first embodiment. In visual appearance, it is identical with the endoscopic auditory canal cleaning apparatus 1 of the first embodiment. Since it requires the ear picking main body 10 to be rotated in itself, however, it differs in the construction of the leading terminal of the ear picking device from the apparatus of the first embodiment. The following description, therefore, covers solely the leading terminal of the ear picking device and leaves out the other components of the apparatus by regarding them identical with the corresponding components of the apparatus of the first embodiment. In FIG. 19, the component elements which are likewise found in the first embodiment are denoted by identical reference numerals. FIG. 19, similarly to FIG. 5, is a cross section of the ear picking device taken along the line A—A.

The ear pick mounting part 40, as illustrated in FIG. 19, has a gear holder 150 embedded therein in the place of the light source holder 82A shown in FIG. 5. The gear holder 150, similarly to the light source holder 82A, is embedded in the ear pick mounting part 40. The gear holder 150 and the ear pick mounting part 40 jointly have a planet gear 151 nipped therebetween.

The planet gear 151 is held rotatably by the gear holder 150 lest it should fall down into the inner empty space 80 of the holding part 5. The planet gear 151 has a through hole formed in the rotational axis thereof. The through hole is so formed as to be converged from the leading terminal side to the basal terminal side of the ear picking device 2. An ear picking main body 160 is inserted into the through hole till it is fixed therein.

The ear picking main body 160 is composed of an inserting part 162 intended to be inserted into the ear pick mounting part 40 and a leading terminal part 161 intended to hold the ear picking part 90. The leading terminal part 161, similarly to the first embodiment, serves the purpose of holding the ear picking part 90.

The inserting part 162 has the leading terminal thereof inserted into the through hole of the planet gear 151 till the leading terminal collides against the gear holder 150. The inserting part 162 is formed substantially in the same shape and diameter as the through hole. When the inserting part 162 is inserted into the through hole, therefore, the planet gear 151 is firmly fixed in the ear picking main body 160. To replace the ear picking main body 160, a force is exerted in the direction of extracting the ear picking main body 160 from the ear pick mounting part 40 side. Since the planet gear 151 is held between the ear pick mounting part.40 and the gear holder 150, it cannot be removed from the ear pick mounting part 40 when the ear picking main body 160 is extracted.

A minute gap is interposed between the inserting part 162 of the ear picking main body 160 and an inner wall 43 of the ear pick mounting part 40 in order that the ear picking main body 160 may be rotated in itself. The rotation of the ear picking main body 160 will be described specifically afterward.

The planet gear 151 mentioned above is furnished with a tooth form parallel to the rotational axis thereof. The tooth form of a sun gear 152 is meshed with the tooth form of the planet gear 151. The sun gear 152 is fixed to the protecting pipe 22 which covers the fiber scope 20. The sun gear 152 is firmly fixed as with an adhesive agent lest it should slip on the outer periphery of the protecting pipe 22.

The mechanism for the sun-and-planet motion is materialized by the sun gear 152 and the planet gear 150 mentioned above.

Now, the operation of the endoscopic auditory canal cleaning apparatus contemplated by the second embodiment will be described below.

Similarly to the first embodiment cited above, the user of the endoscopic auditory canal cleaning apparatus inserts the ear picking main body 160 at the leading terminal of the ear picking device 2 and the fiber scope 20 into the auditory canal. The user is enabled by the display device 3 held near at hand to observe the appearance of the interior of the auditory canal.

The user manipulates the ear picking device 2 to guide the ear picking part 90 to the position of cerumen. Here, the user is enabled to rotate the holding part 5 around the image guide 20 as the axis of rotation while keeping hold of part of the holding part of the ear picking device 2 (FIG. 2 refers).

When the user rotates the holding part 5, the planet gear 150 revolves around the axis of the sun gear 152 as the center while the sun gear 152 fixed to the image guide 20 remains in the original position. The planet gear 150 rotates as it revolves because it is meshed with the sun gear 152.

The rotation of the planet gear 150 is transmitted also to the ear picking main body 160 which is held by the planet gear 150. Thus, the ear picking part 90 attached to the ear picking main body 160 also rotates.

As described above, the ear picking part 90 is also rotated as interlocked with the user's operation of rotating the holding part 5. Consequently, the interior of the auditory canal can be cleaned at portions on the ear picking part 90 different from those at which the cleaning was made formerly.

The planet gear mechanism has been described as one example of the mechanism of the movement for rotating the ear picking main body 160. This invention, however, does not need to be limited to the mechanism of the planet gear. By a mechanism different from the mechanism of planet gear, the ear picking main body can be rotated as interlocked with the revolution of the ear picking main body 160 around the image guide 20. Alternatively, the ear picking main body 160 may be singly rotated without being interlocked with the revolution of the ear picking main body 160 induced by the rotation of the holding part 5. By connecting a motor to the ear picking main body 160, for example, the ear picking main body 160 may be enabled to rotate by the power of the rotation of the motor.

By the endoscopic auditory canal cleaning apparatus of this invention, the effects which are described below are attained.

By the endoscopic auditory canal cleaning apparatus according to the first embodiment of this invention, the following effects are obtained.

According to the endoscopic auditory canal cleaning apparatus 1 of this invention, the interior of the auditory canal can be radiated with the light emitted at the leading terminal of the ear picking main body 10 and the image of the interior of the auditory canal can be incorporated by the fiber scope 20 (image incorporating means). Here, the holding part 5 (holding means) for holding the ear picking main body 10 can be freely rotated around the fiber scope 20 as the central axis. It is, therefore, made possible to clean the interior of the auditory canal by freely rotating the ear picking main body 10 alone while keeping the image fixed in one direction. Since the direction of the image is fixed, the interior of the auditory canal can be cleaned safely and infallibly without losing sight of the objective such as cerumen.

This invention particularly befits the removal of wet cerumen because the surface of the ear picking part 90 disposed at the leading terminal of the ear picking main body 10 is covered with a fibrous material and the ear picking part 90 and the ear picking main body 10 therefore fulfill the function of a cotton swab. Since the ear picking main body 10 is so constructed as to guide the light to the leading terminal thereof, it can radiate the interior of the auditory canal brightly in spite of the fact that the leading terminal side of the ear picking main body 10 is covered with the ear picking part 90. Consequently, it is made possible to acquire an image of the interior of the auditory canal.

Further by the attachment of the light guide 30, the interior of the auditory canal can be brightly radiated and the image of the interior of the auditory canal can be easily attained. Since the amount of protrusion of the radiating part 32 of the light guide 30 from the holding part 5 nearly equals the amount of protrusion of the image micro lens 21 of the fiber scope 20 from the holding part 5, the radiating part 32 can properly radiate the interior of the auditory canal without interfering with the incorporation of an image by the image micro lens 21.

Since the interior of the auditory canal is radiated brightly by the light emitted from the light guide 30, the conventionally used cotton-wound type ear pick (cotton swab) can be used in the place of the ear picking main body 10.

Since the ear picking main body 10 is detachable from the holding part 5 and can be replaced with a new supply when it is polluted, it can be used hygienically. Optionally, the ear picking main body 10 may be substituted with the spoon type ear picking main body 130 which is furnished with a scraping part of the shape of a spoon and formed so as to guide the light to the leading terminal or the annular ear picking main body 140 furnished at the leading terminal thereof with a plurality of annular scraping parts and formed so as to guide the light to the leading terminal. Consequently, the removal of dry cerumen can be accomplished.

Further, the ear picking part 90 itself is freely removable from the ear picking main body 10. The ear picking part 90, therefore, can be used hygienically because this ear picking part 90, when polluted with entwined wet cerumen, can be discarded and replaced with a new supply. The ear picking main body 10 proves economical because it can be used again.

The ear picking main body 10 comprises the first engaging part 11 penetrating the through hole 93 while deforming the base 91 and the second engaging part 12 colliding against the end face on the basal terminal side of the base 91 and holds the ear picking part 90 between the first engaging part 11 and the second engaging part 12. The first engaging part 11 and the second engaging part 12 have larger diameters than the through hole 93 of the ear picking part 90. The ear picking part 90, therefore, does not drop off during the process of cleaning the interior of the auditory canal. Since the ear picking part 90 has the base 91 thereof formed of an elastic body, it can be attached to and detached from the ear picking main body 10 while keeping the base 91 deformed elastically.

By furnishing the apparatus with a plurality of light sources 81B, it is made possible to radiate the interior of the auditory canal more brightly. Specifically, the plurality of light sources 81B are so disposed that the beams of light from these light sources may be emitted from the leading terminal face of the ear pick mounting part 40, for example. Here, the emission of the light from the leading terminal face of the mounting part 40 is accomplished by any of the following methods.

One of the methods comprises keeping from attaching anything to the holes to which the light guide 30 or the like is attached. Since the holes do not have anything at all, the beams of light from the light sources 81B directly radiate the interior of the auditory canal through the leading terminal face of the ear pick mounting part 40. Another of the methods comprises substituting the light guide 30 with what is made of the same material as the light guide 30 and extended to the leading terminal face of the ear pick mounting part 40. Consequently, the light is guided to the leading terminal face of the ear pick mounting part 40 and allowed to radiate the interior of the auditory canal.

It is also permissible to provide the apparatus with a plurality of sets of light sources 81B and light guides 30 and have these components held by the holding part 5 so as to be freely rotated around the fiber scope 20 as the central axis. In this case, the interior of the auditory canal can be radiated more brightly to the innermost part thereof by the plurality of light guides 30.

The endoscopic auditory canal cleaning apparatus according to the second embodiment is furnished with the planet gear mechanism in addition to the construction of the endoscopic auditory canal cleaning apparatus of the first embodiment. It, therefore, can accomplish the following effects in addition to the effects which are accomplished by the endoscopic auditory canal cleaning apparatus of the first embodiment.

The mechanism of the sun-and-planet movement enables the ear picking main body 160 and the ear picking part 90 to rotate as interlocked with the user's rotation of the holding part 5. During the user's cleaning of the interior of the auditory canal, therefore, the ear picking part 90 can be wholly used evenly. Since the second embodiment does not allow only one portion of the ear picking part 90 to be used to extremity, it enjoys improvement in the ratio of removal of cerumen by the ear picking part 90 and in the degree of hygiene as compared with the first embodiment. Further, since the ear picking part 90 is used evenly, it is at an advantage in obviating the necessity of replacing the ear picking part 90 on account of extreme pollution of only one portion thereof and consequently proving economical.

The entire disclosure of Japanese Patent Application No. 2003-162942 filed on Jun. 6, 2003 including specification, claims, and summary are incorporated therein by reference in its entirety.

What is claimed is:

1. An endoscopic auditory canal cleaning apparatus comprising:
   a light source for generating light,
   an ear picking main body so formed as to guide the light generated by said light source to the leading terminal thereof,
   an ear picking part furnished with a surface layer made of a fibrous material, said ear picking part being adapted to be disposed in said ear picking main body while exposing said leading terminal,
   an image incorporating means for taking in an image of the interior of the auditory canal radiated by the light guided to the leading terminal of said ear picking main body,
   a display means for displaying the image incorporated by said image incorporating means, and
   a holding means furnished with a hollow mouth to be penetrated by said image incorporating means and allowed to rotate freely around said image incorporating means as the central axis with said ear picking main body kept in a held state.

2. An endoscopic auditory canal cleaning apparatus according to claim 1, which further comprises a light guide for guiding the light generated by said light source to the leading terminal and radiating the interior of the auditory canal.

3. An endoscopic auditory canal cleaning apparatus according to claim 2, wherein the radiating part of said light guide and the image incorporating part of said image incorporating means protrude from said holding means in nearly same amounts.

4. An endoscopic auditory canal cleaning apparatus according to claim 1, wherein said ear picking main body is removable from said holding means.

5. An endoscopic auditory canal cleaning apparatus according to claim 1, wherein said ear picking part is removable from said ear picking main body.

6. An endoscopic auditory canal cleaning apparatus according to claim 5, wherein
   said ear picking part comprises said surface layer and a base having formed therein a through hole for holding said surface layer and allowing insertion therein of said ear picking main body,
   said base is formed of an elastic body, and
   said ear picking main body comprises a first engaging part penetrating said through hole while keeping said base elastically deformed and a second engaging part colliding against the end face on the basal terminal side of said base and holds said ear picking part between said first engaging part and second engaging part.

7. An endoscopic auditory canal cleaning apparatus according to claim 6, wherein said ear picking main body is furnished with an energizing member exerting upon said base the force directed toward expanding said through hole.

8. An endoscopic auditory canal cleaning apparatus according to claim 6, wherein said ear picking main body is furnished between said first engaging part and said second engaging part with an engaging projection for engaging said ear picking part.

9. An endoscopic auditory canal cleaning apparatus according to claim 2, wherein a plurality of said light sources are provided.

10. An endoscopic auditory canal cleaning apparatus according to claim 1, wherein said ear picking part is disposed within the field of view of said image incorporating means.

11. An endoscopic auditory canal cleaning apparatus according to claim 1, wherein
   said image incorporating means is a fiber scope furnished at the leading terminal thereof with an image micro lens and
   said display part causes an image picked up by said image micro lens to be displayed as magnified.

12. An endoscopic auditory canal cleaning apparatus according to claim 1, wherein
   said image incorporating means is an image sensor and
   said display part subjects the signal from said image sensor to image processing and displays the image consequently formed.

13. An endoscopic auditory canal cleaning apparatus according to claim 1, wherein said ear picking main body can be substituted with a spoon-type ear picking main body furnished at the leading terminal thereof with a picking part of the shape of a spoon and formed so as to guide the light to the leading terminal.

14. An endoscopic auditory canal cleaning apparatus according to claim 1, wherein said ear picking main body can be substituted with an annular ear picking main body furnished at the leading terminal thereof with a plurality of annular ear picking parts and formed so as to guide the light to the leading terminal.

15. An endoscopic auditory canal cleaning apparatus according to claim 1, which further comprises a mechanism of movement for causing said ear picking main body revolved around said image incorporating means in consequence of the rotation of said holding means to be rotated as interlocked or not interlocked with said revolution.

16. An endoscopic auditory canal cleaning apparatus comprising:

a light source for generating light, a light guide for guiding the light generated by said light source to the leading terminal thereof and radiating the interior of the auditory canal, a cylindrical ear picking main body, an ear picking part disposed on the outer periphery of the leading terminal of said ear picking main body and furnished with a surface layer made of a fibrous material, an image incorporating means for incorporating an image of the interior of the auditory canal radiated by said light guide, a display means for displaying the image incorporated by said image incorporating means, and a holding means furnished with a hollow mouth to be penetrated by said image incorporating means and allowed to rotate freely around said image incorporating means as the central axis with said ear picking main body kept in a held state.

17. An endoscopic auditory canal cleaning apparatus according to claim 16, wherein the radiating part of said light guide and the image incorporating part of said image incorporating means protrude from said holding means in nearly same amounts.

18. An endoscopic auditory canal cleaning apparatus according to claim 16, wherein said ear picking main body is removable from said holding means.

19. An endoscopic auditory canal cleaning apparatus according to claim 16, wherein a plurality of said light sources are provided.

20. An endoscopic auditory canal cleaning apparatus according to claim 16, wherein said ear picking part is disposed within the field of view of said image incorporating means.

21. An endoscopic auditory canal cleaning apparatus according to claims 16, wherein said image incorporating means is a fiber scope furnished at the leading terminal thereof with an image micro lens and said display part causes an image picked up by said image micro lens to be displayed as magnified.

22. An endoscopic auditory canal cleaning apparatus according to claim 16, wherein said image incorporating means is an image sensor and said display part subjects the signal from said image sensor to image processing and displays the image consequently formed.

23. An endoscopic auditory canal cleaning apparatus according to claim 16, wherein said ear picking main body can be substituted with a spoon-type ear picking main body furnished at the leading terminal thereof with a picking part of the shape of a spoon and formed so as to guide the light to the leading terminal.

24. An endoscopic auditory canal cleaning apparatus according to claim 16, wherein said ear picking main body can be substituted with an annular ear picking main body furnished at the leading terminal thereof with a plurality of annular ear picking parts and formed so as to guide the light to the leading terminal.

25. An endoscopic auditory canal cleaning apparatus according to claims 16, which further comprises a mechanism of movement for causing said ear picking main body revolved around said image incorporating means in consequence of the rotation of said holding means to be rotated as interlocked or not interlocked with said revolution.

26. An endoscopic apparatus for cleaning an auditory canal, said apparatus comprising:

a light source for generating light, an ear picking main body so formed as to guide the light generated by said light source to the leading terminal thereof, an elastically-deformable, tubular, ear-picking part having a through-hole and an outer layer made of fibrous material, said deformable, tubular, ear-picking part being removably attached over said ear-picking main body so as to leave said leading terminal of said ear-picking main body exposed and capable of providing illumination;

a fiber scope having a micro-lens and being adapted to take an image of the interior of the auditory canal using said illumination provided via said exposed leading terminal of said ear picking main body;

a display means for displaying the image taken by said fiber scope, and a holding means furnished with a hollow mouth to be penetrated by said fiber scope, and allowed to rotate freely around said fiber scope, with the central axis of the fiber scope being the axis of the rotation.

27. An endoscopic apparatus for cleaning an auditory canal, said apparatus comprising:

a light source for generating light, a light guide for guiding the light generated by said light source to the leading terminal thereof and radiating the interior of the auditory canal, an ear picking main body having one or more annular protrusions, an elastically-deformable, tubular, ear-picking part having a through-hole and an outer layer made of fibrous material, said deformable, tubular, ear-picking part being removably attached over said annular protrusions of said ear picking main body;

a fiber scope having a micro-lens and being adapted to take an image of the interior of the auditory canal using said illumination provided via said exposed leading terminal of said ear picking main body;

a display means for displaying the image taken by said fiber scope, and a holding means furnished with a hollow mouth to be penetrated by said fiber scope, and allowed to rotate freely around said fiber scope, with the central axis of the fiber scope being the axis of the rotation.

* * * * *